US 7,432,959 B2

United States Patent
Ueda (10) Patent No.: US 7,432,959 B2
(45) Date of Patent: Oct. 7, 2008

(54) IMAGE ACQUIRING DEVICE AND METHOD CAPABLE OF PERFORMING OPTIMUM TIME LAPSE IMAGING EASILY

(75) Inventor: Hitoshi Ueda, Hachioji (JP)

(73) Assignee: Olympus Corporation, Tokyo (JP)

( * ) Notice: Subject to any disclaimer, the term of this patent is extended or adjusted under 35 U.S.C. 154(b) by 822 days.

(21) Appl. No.: 10/768,884

(22) Filed: Jan. 29, 2004

(65) Prior Publication Data

US 2004/0183921 A1  Sep. 23, 2004

(30) Foreign Application Priority Data

Jan. 30, 2003  (JP) .............................. 2003-022359

(51) Int. Cl.
- *H04N 7/18* (2006.01)
- *H04N 9/47* (2006.01)
- *H04N 58/228* (2006.01)
- *H04N 5/222* (2006.01)
- *H04N 5/225* (2006.01)
- *G03B 7/083* (2006.01)
- *G03B 17/18* (2006.01)

(52) U.S. Cl. ................. 348/221.1; 348/79; 348/333.02; 396/246; 396/287

(58) Field of Classification Search ............ 348/333.02, 348/222.1, 79
See application file for complete search history.

(56) References Cited

U.S. PATENT DOCUMENTS

| 4,519,692 A | * | 5/1985 | Michalik ..................... 396/48 |
| 5,196,938 A | * | 3/1993 | Blessinger .................. 348/22 |
| 2003/0016301 A1 | * | 1/2003 | Aizaki et al. ................ 348/345 |
| 2003/0197795 A1 | * | 10/2003 | Schinner ..................... 348/255 |

FOREIGN PATENT DOCUMENTS

JP  11-112852 A  4/1999

* cited by examiner

*Primary Examiner*—Tuan Ho
*Assistant Examiner*—Tuan H Le
(74) *Attorney, Agent, or Firm*—Frishauf, Holtz, Goodman & Chick, P.C.

(57) ABSTRACT

An imaging portion performs imaging of a subject. A time lapse imaging condition setting portion sets a time lapse imaging condition including at least an exposure time and an imaging interval, prior to the imaging of the subject by the imaging portion. A determining portion determines a contradiction of the time lapse imaging condition set by the time lapse imaging condition setting portion according to a predetermined criterion. A presenting portion presents at least information relating to the contradiction of the time lapse imaging condition based on a determined result by the determining portion.

6 Claims, 7 Drawing Sheets

IMAGE ACQUIRING DEVICE AND METHOD CAPABLE OF PERFORMING OPTIMUM TIME LAPSE IMAGING EASILY

CROSS-REFERENCE TO RELATED APPLICATIONS

This application is based upon and claims the benefit of priority from the prior Japanese Patent Application No. 2003-022359, filed Jan. 30, 2003, the entire contents of which are incorporated herein by reference.

BACKGROUND OF THE INVENTION

1. Field of the Invention

The present invention relates to an image acquiring device and method for performing a time lapse imaging function, and more particularly to an image acquiring device and method having a time lapse imaging function capable of selecting an optimum imaging method easily.

2. Description of the Related Art

Hitherto is known an image acquiring device having a time lapse imaging function for taking and recording images automatically at specific time intervals, and, for example, an imaging device (digital still camera) disclosed in Patent Document 1 (Jpn. Pat. Appln. KOKAI Publication No. 11-112852) is known.

Such an imaging device having a time lapse imaging function is often used in a microscopic image acquiring device for taking time course changes of, for example, live cells.

The digital still camera disclosed in Patent Document 1 is designed to repeat the operation of imaging after lapse of a predetermined time interval, and imaging again after the predetermined time interval in end of the imaging.

Figure 9:
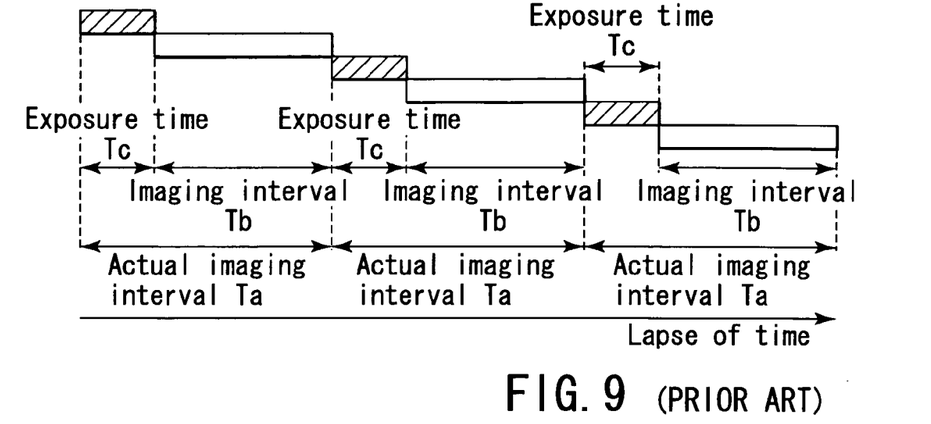
FIG. 9 is a diagram for explaining a conventional time lapse imaging method.

FIG. 9 is a diagram explaining the operation of the time lapse imaging in a prior art.

In this case, the actual imaging interval Ta is the sum of an imaging interval Tb designated by an operator and an exposure time Tc.

Even if the imaging interval Ta is set by summing up the imaging interval Tb and exposure time Tc, there is no problem in general photography of extremely short exposure times ranging from ten thousandths of a second to tenths of a second.

However, in the above-described microscopic image acquiring device for taking time course changes of live cells, generally, fluorescence photography is employed.

In such a microscopic image acquiring device by fluorescence photography, since a subject of an extremely low luminance is taken, the exposure time is very long, ranging from several seconds to tens of seconds.

Therefore, when time lapse imaging as shown in FIG. 9 is applied in the microscopic image acquiring device by fluorescence photography, assuming that the sum of the imaging interval Tb designated by the operator and the exposure time Tc is set as the actual imaging interval Ta, the actual imaging interval Ta may be largely different from the imaging interval intended by the operator, and the subject may not be taken as desired by the operator.

Figure 10:
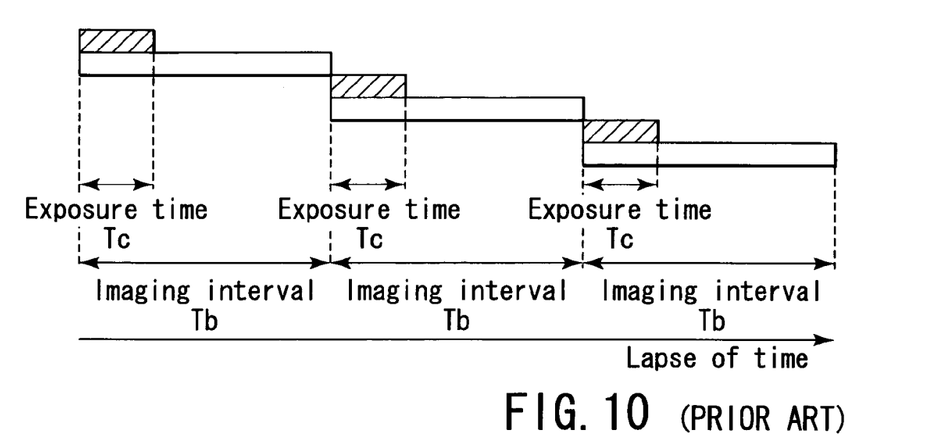
FIG. 10 is a diagram for explaining another conventional time lapse imaging method.

FIG. 10 is a diagram for explaining the operation of time lapse imaging by another prior art devised to solve the above problems.

In this imaging technique, by including the exposure time Tc in the imaging interval Tb designated by the operator, imaging can be started at every predetermined time interval Tb regardless of the exposure time Tc.

However, if the exposure time Tc is intended to be included in the imaging interval Tb designated by the operator, various contradictory states may result.

Figure 11:
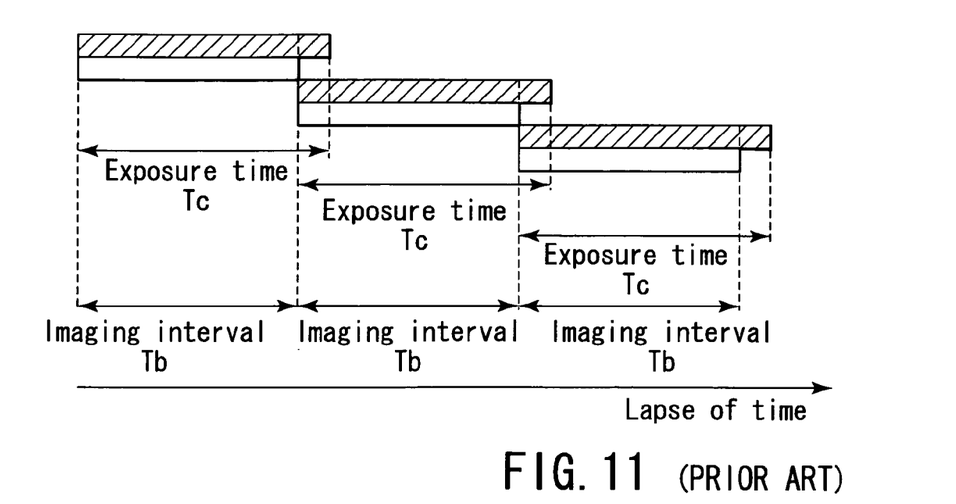
FIG. 11 is a diagram for explaining a contradiction of an imaging condition in the conventional time lapse imaging.

FIG. 11 is a diagram for explaining an example of a contradictory state occurring in the time lapse imaging by such another prior art.

In this example, the contradiction is that the exposure time Tc determined by automatic exposure or determined manually may be longer than the imaging interval Tb set by the operator (exposure time Tc≧imaging interval Tb).

In such a contradictory state, each exposure time Tc itself is overlapped in time, and time lapse imaging is disabled.

In order to avoid such a contradiction in time lapse imaging, hitherto, by using a user interface (UI), for example, it is proposed to limit as follows:

(1) the imaging interval may not be shorter than the exposure time during setting of imaging interval, or (2) the exposure time may not be longer than the imaging interval during setting of exposure time.

Generally, however, in time lapse imaging, the important item differs with the purpose of photography, such as photography with emphasis on the exposure time or photography with emphasis on the imaging interval, and such limitation by the UI makes it difficult for the operator to select the imaging method, or is likely to lead to operation errors.

BRIEF SUMMARY OF THE INVENTION

According to a first aspect of the present invention, there is provided an image acquiring device for performing time lapse imaging, comprising:

an imaging portion which performs imaging of a subject;

a time lapse imaging condition setting portion which sets a time lapse imaging condition including at least an exposure time and an imaging interval, prior to the imaging of the subject by the imaging portion;

a determining portion which determines a contradiction of the time lapse imaging condition set by the time lapse imaging condition setting portion according to a predetermined criterion; and a presenting portion which presents at least information relating to the contradiction of time lapse imaging condition based on a determined result by the determining portion.

According to a second aspect of the present invention, there is provided an image acquiring device for performing time lapse imaging according to the first aspect, wherein the determining portion determines the contradiction of the time lapse imaging condition by using a relation between the exposure time and the imaging interval as the predetermined criterion.

According to a third aspect of the present invention, there is provided an image acquiring device for performing time lapse imaging according to the second aspect, further comprising:

an avoiding condition generating portion which generates a plurality of time lapse imaging conditions for avoiding the contradiction of the time lapse imaging condition based on the determined result by the determining portion, and causes to present information relating to the plurality of time lapse imaging conditions by the presenting portion;

a selecting portion which selects one of time lapse imaging condition from within the information relating to the plurality of time lapse imaging conditions presented by the presenting portion; and an instructing portion which instructs the imaging portion to execute time lapse imaging based on the time lapse imaging condition selected by the selecting portion.

According to a fourth aspect of the present invention, there is provided an image acquiring device for performing time lapse imaging according to the third aspect, further comprising:

an exposure time setting portion which sets the exposure time set by the time lapse imaging condition setting portion to the imaging portion; and a gain setting portion which enables setting of gain of an output signal from the imaging portion, wherein, when the determining portion determines the contradiction of the time lapse imaging condition in which the exposure time is longer than the imaging interval, the avoiding condition generating portion changes a set value of the exposure time by the exposure time setting portion to an exposure time shorter than the imaging interval, and sets a value of the gain set by the gain setting portion based on a value determined from a ratio of the exposure time after change and the imaging interval.

According to a fifth aspect of the present invention, there is provided an image acquiring device for performing time lapse imaging according to the third aspect, further comprising:

an exposure time setting portion which sets the exposure time set by the time lapse imaging condition setting portion to the imaging portion; and a brightness correcting portion which enables correction of brightness of an image by an output signal from the imaging portion, wherein, when the determining portion determines the contradiction of the time lapse imaging condition in which the exposure time is longer than the imaging interval, the avoiding condition generating portion changes a set value of the exposure time by the exposure time setting portion to an exposure time shorter than the imaging interval, and sets a value for correcting the brightness of the image by the brightness correcting portion based on a value determined from a ratio of the exposure time after change and the imaging interval.

According to a sixth aspect of the present invention, there is provided an image acquiring device for performing time lapse imaging according to the third aspect, further comprising:

an exposure time setting portion which sets the exposure time set by the time lapse imaging condition setting portion to the imaging portion;

a gain setting portion which enables setting of gain of an output signal from the imaging portion; and a brightness correcting portion which enables correction of brightness of an image by the output signal from the imaging portion, wherein, when the determining portion determines the contradiction of the time lapse imaging conditions in which the exposure time is longer than the imaging interval, the avoiding condition generating portion changes a set value of the exposure time by the exposure time setting portion to an exposure time shorter than the imaging interval, and sets a value of the gain set by the gain setting portion to a value determined from a ratio of the exposure time after change and the imaging interval, and when a set gain value exceeds a maximum gain value, sets the maximum gain value as the value of the gain set by the gain setting portion and sets a value for correcting the brightness of the image by the brightness correction part based on a value determined from a ratio of the value of the gain determined from the ratio and the maximum gain value.

According to a seventh aspect of the present invention, there is provided an image acquiring device for performing time lapse imaging according to the first aspect, wherein the imaging portion includes an imaging portion of a microscopic image acquiring device.

According to an eighth aspect of the present invention, there is provided an image acquiring method for performing time lapse imaging, comprising:

preparing an imaging portion which performs imaging of a subject;

setting a time lapse imaging condition including at least an exposure time and an imaging interval, prior to the imaging of the subject by the imaging portion;

determining a contradiction of the time lapse imaging condition set by including at least the exposure time and the imaging interval according to a predetermined criterion; and presenting at least information relating to the contradiction of the time lapse imaging condition based on a determined result of the contradiction of the time lapse imaging condition, by a presenting portion.

According to a ninth aspect of the present invention, there is provided an image acquiring method for performing time lapse imaging according to the eighth aspect, wherein the determining determines the contradiction of the time lapse imaging condition by using a relation between the exposure time and the imaging interval as the predetermined criterion.

According to a tenth aspect of the present invention, there is provided an image acquiring method for performing time lapse imaging according to the ninth aspect, further comprising:

generating a plurality of time lapse imaging conditions for avoiding the contradiction of the time lapse imaging condition based on the determined result of the contradiction of the time lapse imaging condition, and presenting information relating to the plurality of time lapse imaging conditions by the presenting portion;

selecting one of time lapse imaging condition from within the information relating to the plurality of time lapse imaging conditions presented by the presenting portion; and instructing the imaging portion to execute time lapse imaging based on the time lapse imaging condition selected from within the plurality of time lapse imaging conditions.

According to an eleventh aspect of the present invention, there is provided an image acquiring method for performing time lapse imaging according to the tenth aspect, further comprising:

preparing an exposure time setting portion which sets the exposure time by the setting of the time lapse imaging condition to the imaging portion; and preparing a gain setting portion which enables setting of gain of an output signal from the imaging portion, wherein, when the determining determines the contradiction of the time lapse imaging condition in which the exposure time is longer than the imaging interval, the generating the plurality of time lapse imaging conditions changes a set value of the exposure time by the exposure time setting portion to an exposure time shorter than the imaging interval, and sets a value of the gain set by the gain setting portion based on the value of the gain determined from a ratio of the exposure time after change and the imaging interval.

According to a twelfth aspect of the present invention, there is provided an image acquiring method for performing time lapse imaging according to the tenth aspect, further comprising:

preparing an exposure time setting portion which sets the exposure time by the setting of the time lapse imaging condition to the imaging portion; and preparing a brightness correcting portion which enables correction of brightness of an image by an output signal from the imaging portion, wherein, when the determining determined the contradiction of the time lapse imaging condition in which the exposure time is longer than the imaging interval, the generating the plurality of time lapse imaging conditions changes a set value of the exposure time by the exposure time setting portion to an exposure time shorter than the imaging interval, and sets a value for correcting the brightness of the image by the brightness correcting portion based on a value determined from a ratio of the exposure time after change and the imaging interval.

According to a thirteenth aspect of the present invention, there is provided an image acquiring method for performing time lapse imaging according to the tenth aspect, further comprising:

preparing an exposure time setting portion which sets the exposure time by the setting of the time lapse imaging condition to the imaging portion;

preparing a gain setting portion which enables setting of gain of an output signal from the imaging portion; and preparing a brightness correcting portion which enables correction of brightness of an image by the output signal from the imaging portion, wherein, when the determining determines the contradiction of the time lapse imaging condition in which the exposure time is longer than the imaging interval, the generating the plurality of time lapse imaging conditions changes a set value of the exposure time by the exposure time setting portion to an exposure time shorter than the imaging interval, and sets a value of the gain set by the gain setting portion to a value determined from a ratio of the exposure time after change and the imaging interval, and when a set gain value exceeds a maximum gain value, sets the maximum gain value as the value of the gain set by the gain setting portion and sets a value for correcting the brightness of the image by the brightness correcting portion based on a value determined from a ratio of the value of the gain determined from the ratio and the maximum gain value.

According to a fourteenth aspect of the present invention, there is provided an image acquiring method for performing time lapse imaging according to the eighth aspect, wherein the imaging portion includes an imaging portion of a microscopic image acquiring device for fluorescence photography.

According to a fifteenth aspect of the present invention, there is provided an image acquiring device for performing time lapse imaging, comprising:

imaging means for performing imaging of a subject;

time lapse imaging condition setting means for setting a time lapse imaging condition including at least an exposure time and an imaging interval, prior to the imaging of the subject by the imaging means;

determining means for determining a contradiction of the time lapse imaging condition set by the time lapse imaging condition setting means according to a predetermined criterion; and presenting means for presenting at least information relating to the contradiction of the time lapse imaging condition based on a determined result by the determining means.

According to a sixteenth aspect of the present invention, there is provided an image acquiring device for performing time lapse imaging according to the fifteenth aspect, wherein the determining means determines the contradiction of the time lapse imaging condition by using a relation between the exposure time and the imaging interval as the predetermined criterion.

According to a seventeenth aspect of the present invention, there is provided an image acquiring device for performing time lapse imaging according to the sixteenth aspect, further comprising:

avoiding condition generating means for generating a plurality of time lapse imaging conditions for avoiding the contradiction of the time lapse imaging condition based on the determined result by the determining means, and causing to present information relating to the plurality of time lapse imaging conditions by the presenting means;

selecting means for selecting one of time lapse imaging condition from within the information relating to the plurality of time lapse imaging conditions presented by the presenting means; and instructing means for instructing the imaging means to execute time lapse imaging based on the time lapse imaging condition selected by the selecting means.

According to an eighteenth aspect of the present invention, there is provided an image acquiring device for performing time lapse imaging according to the seventeenth aspect, further comprising:

exposure time setting means for setting the exposure time set by the time lapse imaging condition setting means to the imaging means; and gain setting means for enabling setting of gain of an output signal from the imaging means, wherein, when the determining means determines the contradiction of the time lapse imaging condition in which the exposure time is longer than the imaging interval, the avoiding condition generating means changes a set value of the exposure time by the exposure time setting means to an exposure time shorter than the imaging interval, and sets a value of the gain set by the gain setting means based on the value determined from a ratio of the exposure time after change and the imaging interval.

According to a nineteenth aspect of the present invention, there is provided an image acquiring device for performing time lapse imaging according to the seventeenth aspect, further comprising:

exposure time setting means for setting the exposure time set by the time lapse imaging condition setting means to the imaging means; and brightness correcting means for enabling correction of brightness of an image by an output signal from the imaging means, wherein, when the determining means determines the contradiction of the time lapse imaging condition in which the exposure time is longer than the imaging interval, the avoiding condition generating means changes a set value of the exposure time by the exposure time setting means to an exposure time shorter than the imaging interval, and sets a value for correcting the brightness of the image by the brightness correcting means based on a value determined from a ratio of the exposure time after change and the imaging interval.

According to a twentieth aspect of the present invention, there is provided an image acquiring device for performing time lapse imaging according to the seventeenth aspect, further comprising:

exposure time setting means for setting the exposure time set by the time lapse imaging condition setting means to the imaging means;

gain setting means for enabling setting of gain of an output signal from the imaging means; and brightness correcting means for enabling correction of brightness of the image by the output signal from the imaging means, wherein, when the determining means determines the contradiction of the time lapse imaging condition in which the exposure time is longer than the imaging interval, the avoiding condition generating means changes a set value of the exposure time by the exposure time setting means to an exposure time shorter than the imaging interval, and sets a value of the gain set by the gain setting means to the value determined from a ratio of the exposure time after change and the imaging interval, and when a set gain value exceeds a maximum gain value, sets the maximum gain value as the value of the gain set by the gain setting means and sets a value for correcting the brightness of the image by the brightness correction means based on the value determined from a ratio of the value of the gain determined from the ratio and the maximum gain value.

According to a twenty-first aspect of the present invention, there is provided an image acquiring device for performing time lapse imaging according to the fifteenth aspect, wherein the imaging means includes imaging means of a microscopic image acquiring device.

According to the invention described above, when there is a contradiction of an imaging condition in time elapse imaging, at least information relating to the contradiction of the time elapse imaging condition is presented to an operator, and further an imaging method by a plurality of time elapse imaging conditions for avoiding the contradiction of the time elapse imaging condition is presented. Therefore, the operator can avoid the contradiction of the time elapse imaging condition and select an optimum imaging method easily.

Further, according to the invention, in the case where imaging of giving priority to imaging interval is important, when exposure time at the time of time elapse imaging set by the operator is longer than the imaging interval, it is possible to change the actual exposure time to be less than the imaging interval, and execute imaging by correcting the brightness of an image.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the present invention.

DETAILED DESCRIPTION OF THE INVENTION

Reference will now be made in detail to the embodiments of the invention as illustrated in the accompanying drawings, in which like reference numerals designate like or corresponding parts.

Referring now to the drawings, embodiments of an image acquiring device for performing time lapse imaging of the invention will be described below.

First Embodiment

Figure 1:
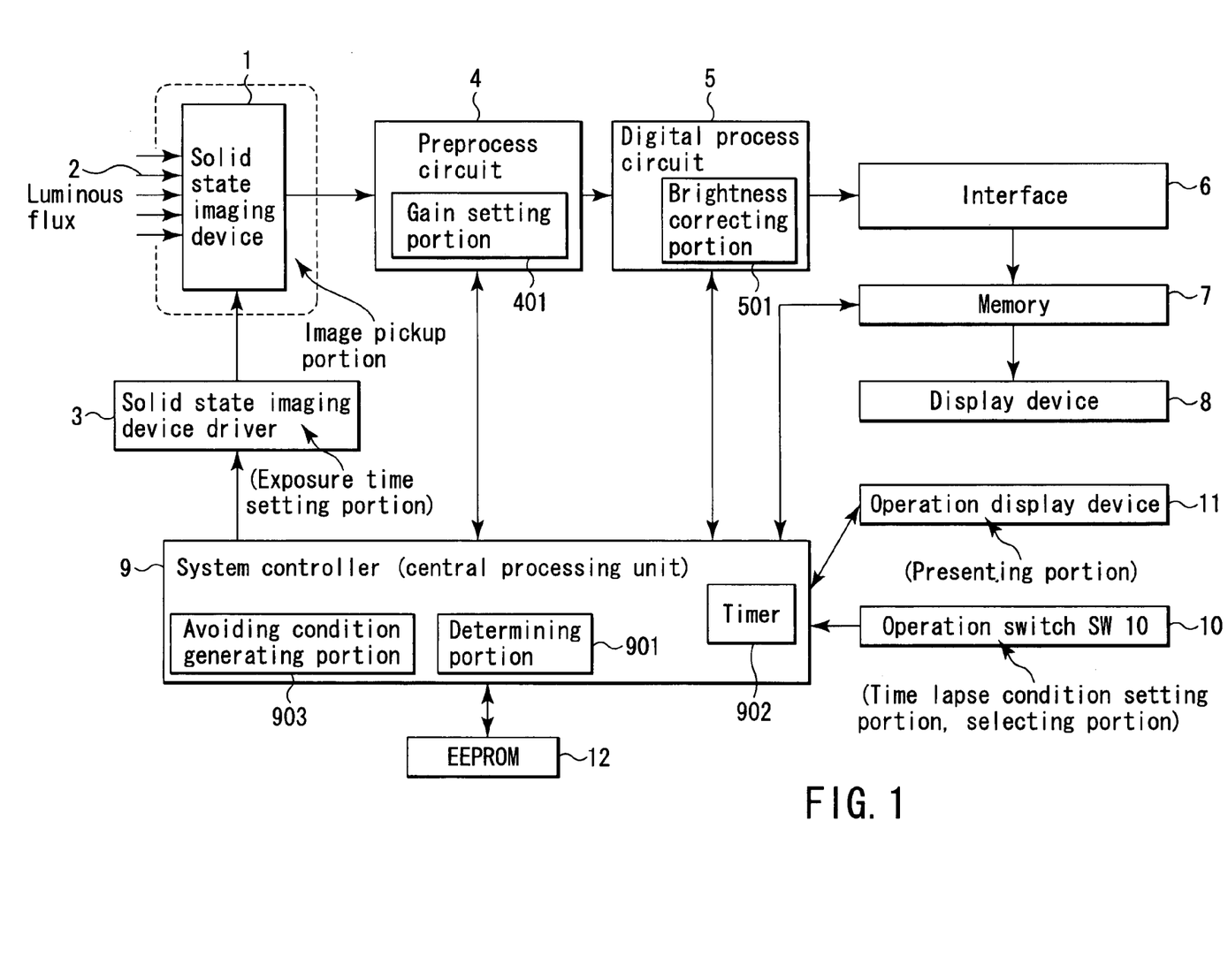
FIG. 1 is a block diagram showing a schematic configuration of a microscopic image acquiring device which is applied as an image acquiring device for performing time lapse imaging according to a first embodiment of the invention.

FIG. 1 is a block diagram showing a schematic configuration of a microscopic image acquiring device which is applied as an image acquiring device for performing time lapse imaging according to a first embodiment of the invention.

In FIG. 1, reference numeral 1 is a solid state imaging device such as a CCD as an imaging portion (means) of the microscopic image acquiring device for fluorescence photography.

In such a microscopic image acquiring device, for example, when taking time course changes of live cells, an exposure time is often very long, from several seconds to tens of seconds, in order to image the subject of an extremely low luminance by fluorescence photography.

On the imaging plane of the solid state imaging device 1, a luminous flux 2 of an observed image of the subject (not shown) is entered.

A solid state imaging device driver 3 for generating a timing signal is connected to the solid state imaging device 1 as exposure time setting means.

Therefore, the solid state imaging device 1 is driven by the exposure time based on the timing signal generated in the solid state imaging device driver 3, takes the subject image, and issues an image signal.

A preprocess circuit 4 is connected to the solid state imaging device 1.

The preprocess circuit 4 includes a gain setting portion 401 for enabling setting of the gain of an output signal of the solid state imaging device 1 by gain increase or the like according to an instruction from a system controller 9 described below, and an A/D converter (not shown) for converting an analog signal into a digital signal to be outputted.

A digital process circuit 5 is connected to the preprocess circuit 4.

The digital process circuit 5 includes a brightness correcting portion (means) 501 for generating a color signal from the digital signal outputted from the preprocess circuit 4, processing matrix conversion, performing various digital processes, and further correcting the brightness of the image according to a parameter designated from the system controller 9 described below.

A memory 7 and a display device 8 are connected to the digital process circuit 5 by way of an interface 6.

The interface 6 is for storing the digital images outputted from the digital process circuit 5 into the memory 7.

The images stored in the memory 7 are shown in the display device 8.

In this example, the memory 7 and display device 8 are connected to the interface 6, but the images may be also transmitted to another image recording device or image display device by way of, for example, a PCI bus or the like.

A system controller (CPU) 9 is connected as control means to the solid state imaging device driver 3, preprocess circuit 4, digital process circuit 5, and memory 7.

The system controller (CPU) 9 is designed to control comprehensively the solid state imaging device driver 3, preprocess circuit 4, digital process circuit 5, and memory 7.

The system controller (CPU) 9 comprises operation switches (SW) 10 including various type of switches, an operation display device 11 for displaying an operation state and a mode state, and also serving as a presenting portion (means) for displaying a contradiction of time lapse imaging conditions, and a nonvolatile memory (EEPROM) 12 for storing information of various settings and the like.

The operation switches SW (10) include, as a time elapse imaging condition setting portion (means), switches for setting conditions relating to imaging such as exposure time, imaging interval, and imaging quantity, and also switches for selecting desired process from plural time lapse imaging conditions presented as the selecting means.

The system controller (CPU) 9 is for comprehensive control of the entire microscopic image acquiring device, and is designed to control driving of the solid state imaging device 1 by the solid state imaging device driver 3, read out the exposure (accumulation of electric charge) and signal, input this signal into the digital process circuit 5 through the preprocess circuit 4, perform various signal processings, and store into the memory 7 by way of the interface 6.

The system controller (CPU) 9 also controls reading of the memory 7, reads the stored image, and names and saves the image in the nonvolatile memory (EEPROM) 12.

The system controller (CPU). 9 includes a determining portion (means) 901, a timer 902, and an avoiding condition generating portion (means) 903.

The determining portion 901 determines the contradiction of time lapse imaging condition about imaging such as exposure time, imaging interval, and imaging quantity determined by the operation switches (SW) 10, based on a predetermined criterion prepared in the determining portion 901.

Herein, the determining portion 901 determines the contradiction of the time lapse imaging condition by using the relation between the exposure time and the imaging interval as mentioned below as the predetermined criterion.

The timer 902 has a function of generating an interrupt process at every predetermined time determined by the system controller (CPU) 9.

The avoiding condition generating portion 903 generates a plurality of time lapse imaging conditions for avoiding the contradiction of the time lapse imaging condition including "process 1", "process 2" and "process 3" mentioned below based on the determining result by the determining portion 901, and also presents information relating to the plurality of time lapse imaging conditions by the operation display device 11.

The system controller (CPU) 9 also has a function as an instructing portion (means) for instructing execution (stop) of various time lapse imaging operations mentioned below on the solid state imaging device 1.

Next, the operation of the first embodiment having such a configuration will be explained in the flowchart in FIG. 2.

First of all, the operator sets the time lapse imaging condition about imaging, such as exposure time, imaging interval and imaging quantity by using the operation switches (SW) 10 as the time lapse imaging condition setting portion.

The system controller (CPU) 9, based on the setting by the operation switches (SW) 10, sets the exposure time in the solid state imaging device driver 3 as the exposure time setting portion (step S101).

In this state, step S101 remains until imaging start is instructed by the operation switches (SW) 10 (step S102).

When imaging start is instructed by the operation switches (SW) 10, the system controller (CPU) 9 determines in the determining unit 901 whether or not the imaging interval determined by the operator is shorter than the exposure time (imaging interval$\leqq$exposure time) (step S103).

When the relation (imaging interval$\leqq$exposure time) is not established, that is, when there is no contradiction in the time lapse imaging condition (imaging interval>exposure time), the system controller (CPU) 9 instructs the solid state imaging device 1 to execute an ordinary time lapse imaging (step S104).

This ordinary time lapse imaging process is described later.

On the other hand, in step S103, when it is determined that the relation (imaging interval$\leqq$exposure time) is established, that is, when there is a contradiction in the time lapse imaging condition, the system controller (CPU) 9 generates a plurality of time lapse imaging conditions for avoiding the contradiction of the time lapse imaging condition in the avoiding condition generating portion 903, and presents information about the plurality of time lapse imaging conditions so as to be selected by the operator (step S105).

In this case, the avoiding condition setting portion 903 of the system controller (CPU) 9 fetches the imaging method selecting message as the information about the plurality of time lapse imaging conditions for avoiding the contradiction in the time lapse imaging condition preliminarily stored in the EEPROM 12, and displays on the screen of the operation display device 11 as the presenting portion.

Figure 3:
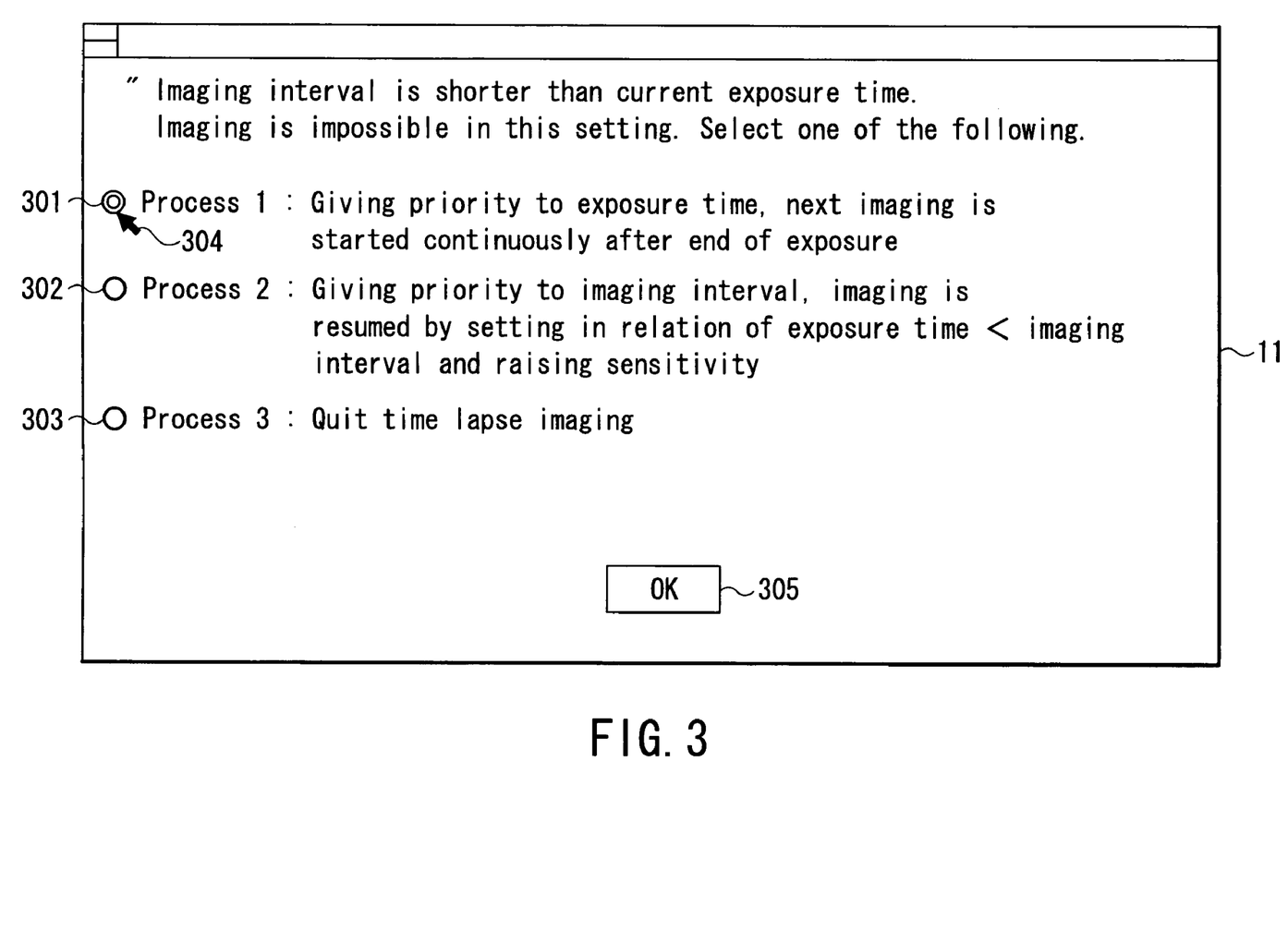
FIG. 3 is a diagram for explaining an imaging method selecting message displayed on a screen of an operation display device in the first embodiment.

Herein, the display message is, for example, as shown in FIG. 3 "Imaging interval is shorter than current exposure time. Imaging is impossible in this setting. Select one of the following.", which is followed by the message of processing method, that is, "process 1" (giving priority to exposure time, next imaging is started continuously after the end of exposure), "process 2" (giving priority to imaging interval, imaging is resumed by setting in relation of exposure time<imaging interval and raising sensitivity), and "process 3" (quit time lapse imaging).

The "process 1", "process 2" and "process 3" on the screen of the operation display device 11 are respectively provided with buttons 301, 302, and 303.

The operator manipulates the operation switch SW 10 as the selecting portion, and moves a cursor 304 on the screen of the operation display device 11 on any one of the buttons 301, 302, 303, and selects by pressing a button (not shown) in the operation switches (SW) 10.

In this case, only one of the buttons 301, 302, 303 can be selected exclusively.

As a result, the operator refers to the message of "process 1", "process 2" or "process 3" as shown in FIG. 3, and manipulates the operation switches (SW) 10 to select any one of the buttons 301, 302, 303 of "process 1", "process 2", "process 3", and moves the cursor 304 onto an OK button 305, and presses a button (not shown) in the operation switches (SW) 10 to establish the selection message of the time lapse imaging.

In the buttons 301, 302, 303 shown in FIG. 3, the double circle mark indicates the selected state, and the single circle mark indicates the non-selected state.

When the operator designates any one of "process 1", "process 2", and "process 3", and the selection is established, the selected message information is noticed from the operation display device 11 to the system controller (CPU) 9.

The system controller (CPU) 9 determines whether or not the selected process is "process 1" (step S106).

When the selected process is determined to be "process 1" shown in FIG. 3, the system controller (CPU) 9 goes to step S109, and instructs the solid state imaging device 1 to execute the time lapse imaging according to "process 1".

When the selected process is not determined to be "process 1" shown in FIG. 3, the system controller (CPU) 9 transfers to the process of step S107.

Again, the system controller (CPU) 9 determines whether or not the selected process is "process 2".

When the selected process is determined to be "process 2" shown in FIG. 3, the system controller (CPU) 9 goes to step S110, and instructs the solid state imaging device 1 to execute the time lapse imaging according to "process 2".

When the selected process is not determined to be "process 2" shown in FIG. 3, the system controller (CPU) 9 transfers to the process of step S108.

Further, the system controller (CPU) 9 determines whether or not the selected process is "process 3".

When the selected process is determined to be "process 3" shown in FIG. 3, the system controller (CPU) 9 goes to step S111, and instructs the solid state imaging device 1 to stop the time lapse imaging process according to "process 3".

In this series of operations, the image acquiring device for performing time lapse imaging executes time lapse imaging corresponding to any one of "process 1", "process 2", and "process 3" as selected by the operator.

In this first embodiment, since it is intended to select any one of "process 1", "process 2", and "process 3", it is not determined to go to No in step S108.

Figure 2:
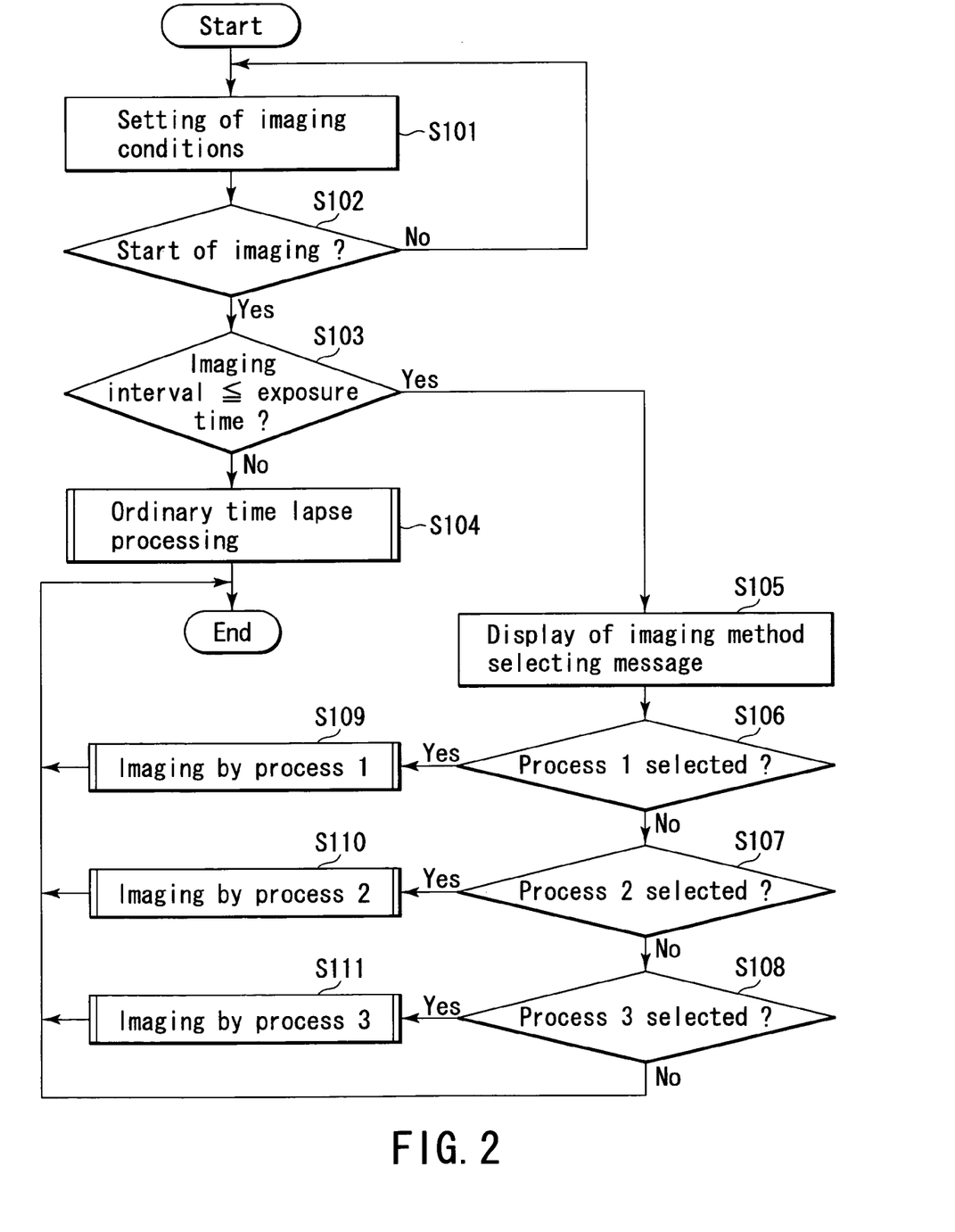
FIG. 2 is a flowchart for explaining the operation of the first embodiment.
Figure 4A:
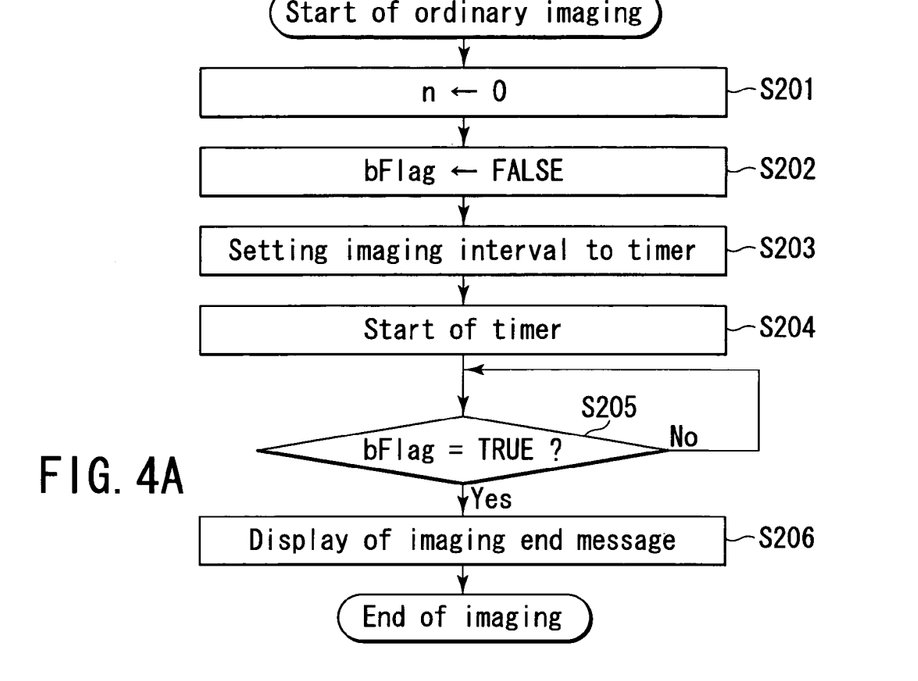
FIGS. 4A and 4B are flowcharts for explaining an ordinary time lapse imaging in the first embodiment.
Figure 4B:
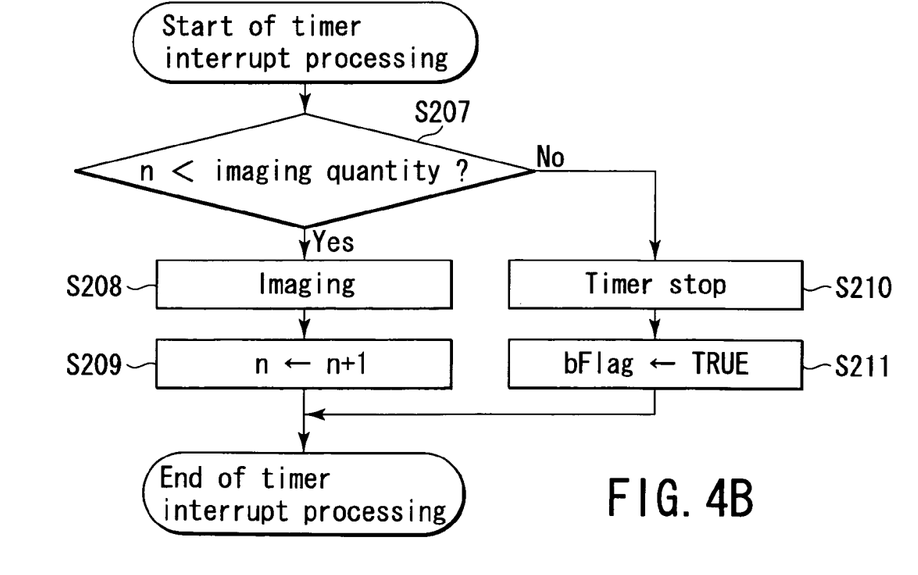

Ordinary time lapse imaging process in step S104 in FIG. 2 is described briefly by referring to the flowcharts in FIGS. 4A and 4B.

Although this ordinary time lapse imaging process is not a feature of the invention, it is necessary for understanding the invention and is explained below.

Variables are used in the following explanation, and these variables refer to variables existing in the register in the system controller (CPU) 9 or in the memory space.

In step S104 shown in FIG. 2, when ordinary time lapse process is called, the system controller (CPU) 9 starts ordinary time lapse imaging process as shown in FIG. 4A.

First, the system controller (CPU) 9 puts 0 in $\underline{n}$ of imaging quantity variable (step S201).

Then, the system controller (CPU) 9 substitutes FALSE for variable bFlag showing end of time lapse imaging (step S202).

Herein, bFlag is controlled to be TRUE at the time of time lapse imaging as described below.

The system controller (CPU) 9 sets the internal timer 902 at the imaging interval set by the operation switches (SW) 10 (step S203), and starts operation of the timer 902 (step S204).

As a result, at every predetermined imaging interval, the timer 902 generates a timer interrupt process.

The system controller (CPU) 9 repeats the process in step S205 until reaching bFlag=TRUE indicating end of time lapse imaging.

In step S205, when bFlag=TRUE indicating end of time lapse imaging is determined, the system controller (CPU) 9 determines that the entire time lapse imaging is complete, and transfers to the process of the next step S206.

In step S206, the system controller (CPU) 9 reads out the message showing the end of imaging from the EEPROM 12, displays the message in the operation display device 11, and instructs the end of imaging to the solid state imaging device 1.

In the midst of repetition of process in step S205, if a timer interrupt process occurs, the system controller (CPU) 9 executes to start the timer interrupt process as shown in FIG. 4B.

The system controller (CPU) 9 determines whether or not the condition of imaging quantity counter variable $\underline{n}$<imaging quantity is established (step S207).

When this condition is established, since the time lapse imaging of all scheduled imaging quantity is not complete, the system controller (CPU) 9 instructs the solid state imaging device 1 to continue imaging (step S208).

In this case, the system controller (CPU) 9 stores the image data taken by the solid state imaging device 1 in the memory 7 by way of the preprocess circuit 4, digital process circuit 5, and interface 6, and displays in the display device 8, and further reads out the image data of the memory 7, and names and stores the data in the EEPROM 12.

When such imaging is over, the system controller (CPU) 9 adds 1 to the imaging quantity counter variable $\underline{n}$ and counts up (step S209), and terminates the timer interrupt process.

On the other hand, in step S207, if the condition of imaging quantity counter variable $\underline{n}$<imaging quantity is not established, the system controller (CPU) 9 determines that the entire imaging is complete and stops the timer 902 (step S210).

Accordingly, timer interrupt process does not occur until the timer 902 starts by the next time lapse imaging.

The system controller (CPU) 9 substitutes TRUE for variable bFlag indicating end of imaging (step S211).

As a result, since the condition of bFlag=TRUE indicating end of time lapse imaging in step S204 is established, the system controller (CPU) 9 transfers from the process in step S205 to the process in step S206.

In this way, in ordinary time lapse imaging, until imaging of all scheduled imaging quantity is over, timer interrupt process occurs at the imaging interval, and by imaging at every occasion of timer interrupt process, ordinary time lapse imaging can be executed.

Figure 5:
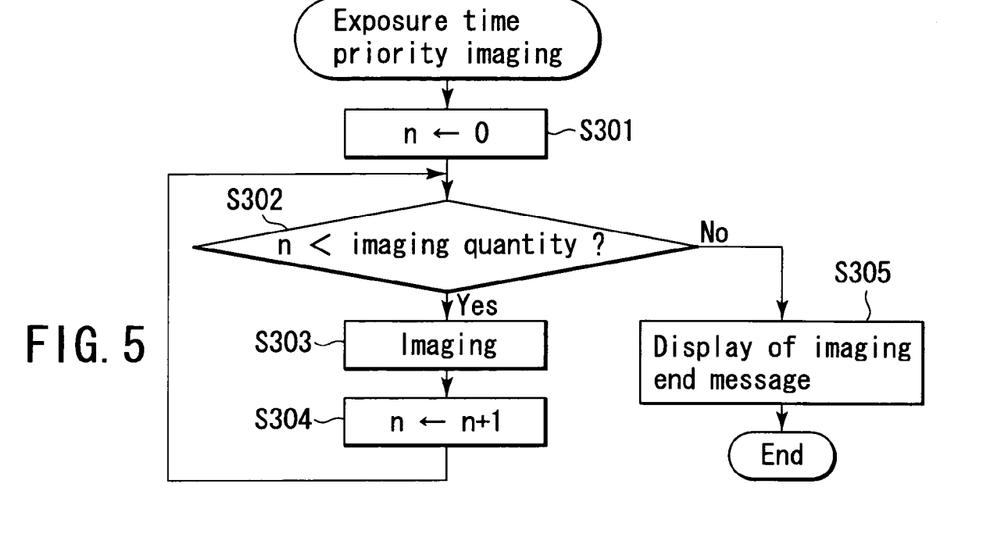
FIG. 5 is a flowchart for explaining an imaging of giving priority to an exposure time in the first embodiment.

The time lapse imaging of "process 1" in step S109 shown in FIG. 2 is explained by referring to the flowchart in FIG. 5.

This "process 1" is, as shown in the message in FIG. 3, for "giving priority to exposure time, next imaging is started continuously after the end of exposure", and this is the process selected when the operator desires to take pictures by giving priority to the exposure time.

In this case, in step S109, when imaging by "process 1" is called, the system controller (CPU) 9 starts exposure time priority imaging as shown in FIG. 5.

The system controller (CPU) 9 clears the imaging quantity counter n to 0 (step S301).

Consequently, the system controller (CPU) 9 compares the imaging quantity counter n and the actual imaging quantity (step S302).

Herein, in the case of $\underline{n}$<actual imaging quantity, since the entire imaging is not complete, the system controller (CPU) 9 starts imaging (step S303).

The imaging in this case is same as the ordinary time lapse imaging mentioned above, and the explanation is omitted.

Thus, when the first imaging is over, the system controller (CPU) 9 adds 1 to the imaging quantity counter $\underline{n}$ and counts up (step S304), returns to the process of step S302, and compares the imaging quantity counter n and the actual imaging quantity.

This operation is repeated until the condition of n<actual imaging quantity is satisfied in the process in step S302.

Thereafter, in step S302, when the condition of n<actual imaging quantity is not satisfied, that is, when the entire imaging is completed, the system controller (CPU) 9 transfers to the process of step S305.

In step S305, the system controller (CPU) 9 reads out the imaging end message preliminarily stored in the EEPROM 12, and displays the message in the operation display device 11.

Thus, in the case of imaging interval≦exposure time, since the next imaging starts every time the imaging end regardless of the imaging interval, the exposure time equivalent to the exposure time designated by the operator is set, and the time lapse imaging emphasizing the exposure time can be executed.

Figure 6:
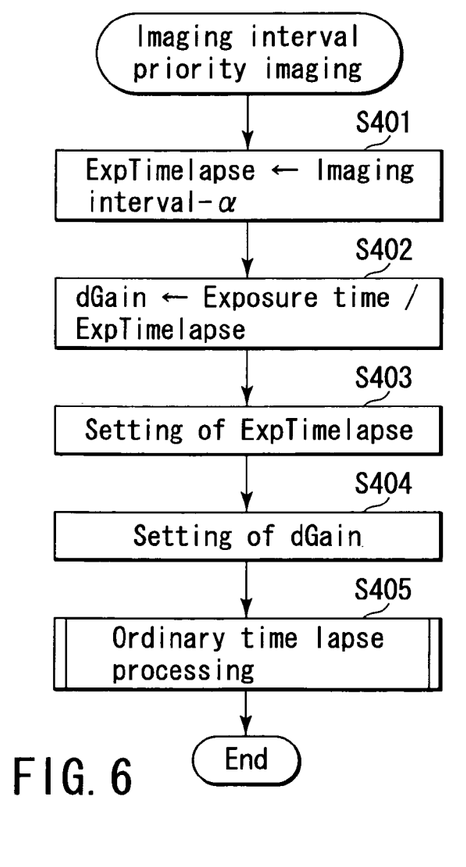
FIG. 6 is a flowchart for explaining an imaging of giving priority to an imaging interval in the first embodiment.

The time lapse imaging of "process 2" in step S110 shown in FIG. 2 is explained by referring to the flowchart in FIG. 6.

This "process 2" is, as shown in message in FIG. 3, for "giving priority to imaging interval, imaging is resumed by setting in relation of exposure time<imaging interval and raising sensitivity", and this is the process selected when the operator desires to take pictures by giving priority to the imaging interval.

In this case, since the priority is given to the imaging interval determined by the operator, the exposure time set by the operator is determined as the actual exposure time and is hence changed to a shorter time than imaging interval, and the taken image obtained is darker by the portion of shortening of the exposure.

In this "process 2", in the gain setting portion 401 of the preprocess circuit 4, by raising the gain of the output signal of the solid state imaging device 1, the sensitivity is raised and the brightness of the taken image is corrected.

In this case, too, when "process 2" is called in step S110, the system controller (CPU) 9 starts the imaging interval priority imaging as shown in FIG. 6.

First, the system controller (CPU) 9 substitutes "imaging interval—α" for variable ExpTimelapse of the exposure time for time lapse imaging in the avoiding condition generating portion 903 (step S401).

Herein, term α is the processing time from end of exposure until the next imaging obtained empirically, and it is a parameter for realizing securely the condition of imaging interval>exposure time.

Next, the system controller (CPU) 9 determines a coefficient dGain for raising the gain of the output signal from the solid state imaging device 1 in the avoiding condition generating portion 903 (step S402).

This coefficient dGain for raising the gain is determined by the division formula of the exposure time/ExpTimelapse.

That is, this coefficient dGain is a coefficient for raising the gain necessary for brightening the image by raising sensitivity by correcting the gain of the output signal from the solid state imaging device 1 because the taken image becomes darker by the shortened time when the exposure time in time lapse imaging is changed to a time shorter than the imaging interval.

Subsequently, the system controller (CPU) 9 sets the exposure time ExpTimelapse having "imaging interval—α" for time lapse imaging in the avoiding condition generating portion 903 in the solid state imaging device driver 3 (step S403).

Next, the system controller (CPU) 9 sets the gain in the gain setting portion 401 of the preprocess circuit 4 determined by the division of the exposure time/ExpTimelapse in the avoiding condition generating portion 903 by the coefficient dGain (step S404).

Then, the system controller (CPU) 9 instructs the solid state imaging device 1 to execute imaging by ordinary time lapse imaging (S405).

Since this process is same as in the ordinary time lapse imaging, its explanation is omitted.

In this way, the exposure time shortened by insertion of "imaging interval—α" is set in the solid state imaging device driver 3, and the gain coefficient for raising the gain for enhancing the sensitivity in response is set in the gain setting portion 401 of the preprocess circuit 4, and by executing the ordinary time lapse imaging by referring to FIGS. 4A and 4B, even if the exposure time is set longer than the imaging interval by the operator, the exposure time less than the imaging interval designated by the operator can be changed automatically, and ultimately the imaging by the imaging interval intended by the operator can be executed.

The exposure amount running short due to shortening of the exposure time can be corrected by raising sensitivity by increasing the gain in the preprocess circuit 4, so that the brightness of the taken image can be maintained favorably.

The "process 3" in step S111 shown in FIG. 2 is explained.

This "process 3" is, as shown in message in FIG. 3, for "quitting time lapse imaging", and this is the process selected when the operator desires to quit time lapse imaging.

In this case, the system controller (CPU) 9 reads out the message showing cancellation of imaging from the EEPROM 12 in the avoiding condition generating part 903, and displays the message in the operation display device 11.

In the first embodiment, as described herein, if there is contradiction in the imaging conditions in the time lapse imaging determined by the operator, a plurality of time lapse imaging conditions for avoiding the contradiction in the time lapse imaging condition are generated and presented to the operator to show information about the plurality of time lapse imaging conditions, so that the operator can select the best time lapse imaging method easily.

In other words, since the time lapse imaging suited to the purpose of the operator can be realized, the image acquiring device for performing time lapse imaging easy to use by the operator can be realized.

In the first embodiment, aside from ordinary time lapse imaging, three types of process, that is, "process 1", "process 2" and "process 3" are prepared as the plurality of time lapse imaging conditions for avoiding the contradiction in the time lapse imaging condition, but the number of processes to be selected is not limited to this example alone.

In the first embodiment, the operator is supposed to set the exposure time, but the image acquiring device for time lapse imaging may be provided with an automatic exposure function, and the invention may be similarly applied if using the exposure time determined by this automatic exposure function.

Furthermore, the EEPROM 12 which is used in the first embodiment may be replaced with other storage devices such as a hard disc or the like.

Second Embodiment

An image acquiring device for performing time lapse imaging according to a second embodiment of the present invention will be described below.

The configuration itself of a microscopic image acquiring device of the second embodiment is same as in FIG. 1, and the following explanation is based on FIG. 1 and its description.

The second embodiment is a process corresponding to a modified example of "process 2" mentioned in the first embodiment.

The process corresponding to the modified example of "process 2" is a process selected when the operator desires to take pictures by giving priority to the imaging interval same as in the first embodiment.

In this case, too, if the exposure time is changed to a shorter time than the imaging interval, the taken image becomes darker by the portion of the shortness of the exposure time.

The sensitivity is raised by correcting the brightness of the taken image by the brightness correcting portion 501 of the digital process circuit 5.

Figure 7:
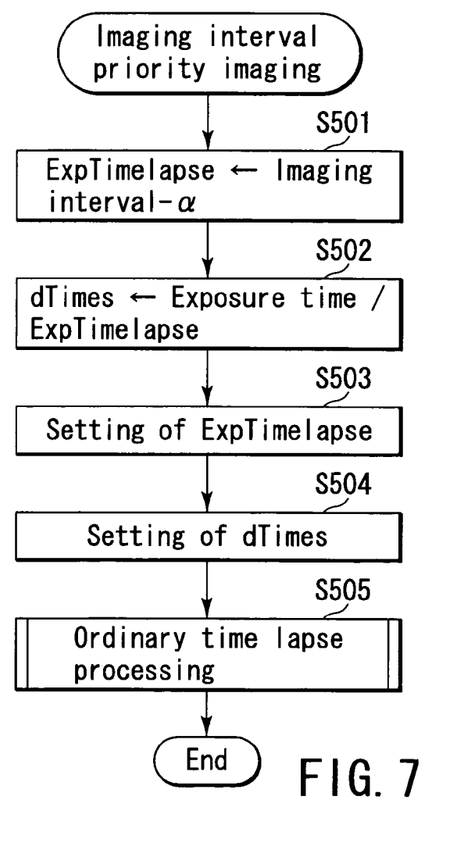
FIG. 7 is a flowchart for explaining an imaging of giving priority to an imaging interval in a second embodiment of the present invention.

In this case, when "process 2" is called in step S110 shown in FIG. 2, the system controller (CPU) 9 starts the imaging time priority imaging as shown in FIG. 7.

The system controller (CPU) 9 substitutes "imaging interval—$\alpha$" for the variable ExpTimelapse of the exposure time for time lapse imaging in the avoiding condition generating portion 903 (step S501).

Herein, $\alpha$ is same as mentioned in the first embodiment, and its explanation is omitted.

The system controller (CPU) 9 determines a coefficient dTimes for multiplying the output signal from the preprocess circuit 4 by the determined coefficient in the avoiding condition generating portion 903 (step S502).

In this case, the coefficient dTimes is determined by the division calculation of the exposure time/ExpTimelapse.

That is, when the exposure time of the time lapse imaging is changed to be shorter than the imaging interval, since the taken image becomes darker by the shortened portion of exposure time, a necessary coefficient is determined to brighten the image by multiplying the output signal from the preprocess circuit by the coefficient and raising sensitivity.

Subsequently, the system controller (CPU) 9 sets the exposure time ExpTimelapse having "imaging interval—$\alpha$" for time lapse imaging in the avoiding condition generating portion 903, in the solid state imaging device driver 3 (step S503).

The system controller (CPU) 9 sets the coefficient dTimes determined by the division of the exposure time/ExpTimelapse in the avoiding condition generating portion 903, in the brightness correcting portion 501 in the digital process circuit 5 (step S504).

The system controller (CPU) 9 instructs the solid state imaging device 1 to execute imaging by ordinary time lapse process (step S505).

Since this process is same as in the foregoing case of the ordinary time lapse imaging, its explanation is omitted.

As a result, the exposure time shortened by putting "imaging interval—$\alpha$" is set in the solid state imaging device driver 3, and the corresponding correction coefficient for raising the sensitivity determined by the division of the exposure time/ExpTimelapse is set in the brightness correcting portion 501 of the digital process circuit 5, and ordinary time lapse imaging in FIGS. 4A and 4B is executed. Therefore, even if the exposure time is set longer than the imaging interval by the operator, it can be automatically corrected to the exposure time less than the imaging interval designated by the operator, so that the time lapse imaging is ultimately executed at the imaging interval intended by the operator.

Lack of exposure due to shortening of the exposure time can be corrected so as to raise the sensitivity by multiplying the brightness by the coefficient in the digital process circuit 5, And hence the brightness of the taken image can be favorably maintained.

Therefore, also in the second embodiment, when the operator desires to image by priority given to the imaging interval, if the exposure time set in time lapse imaging is longer than the imaging interval (exposure time>imaging interval), the actual exposure time is changed to less than the imaging interval, and the sensitivity is raised. Thereby, the time lapse imaging is executed by correcting the brightness, and the image acquiring device for time lapse imaging suited to the purpose of the operator and easy ease of use can be provided.

Since setting of the brightness correcting portion 501 of the digital process circuit 5 is realized by digital processing, brightness correction can be realized easily.

Third Embodiment

An image acquiring device for performing time lapse imaging according to a third embodiment of the present invention will be described below.

The configuration itself of a microscopic image acquiring device of the third embodiment is same as in FIG. 1, and the following explanation is based on FIG. 1 and its description.

The third embodiment is a combination of "process 2" in the first embodiment, and a process corresponding to a modified example of "process 2" in the first embodiment.

That is, in "process 2" in the first embodiment, the gain coefficient to be set in the preprocess circuit 4 is determined from the relation of the shortened exposure time and the imaging interval.

However, if the difference between the imaging interval and the shortened exposure time is large, the obtained gain coefficient may be larger than the gain coefficient that can be set in the preprocess circuit 4 (hereinafter called maximum gain), so that it may not be sufficient for raising the gain by correction by the gain coefficient alone.

In the third embodiment, in such a case, the gain setting portion 401 of the preprocess circuit 4 is set at the maximum gain, and a further insufficient gain portion is compensated by coefficient multiplication of the brightness of the digital image in the brightness correcting portion 501 in the digital process circuit 5, and thereby the sensitivity is raised.

Figure 8:
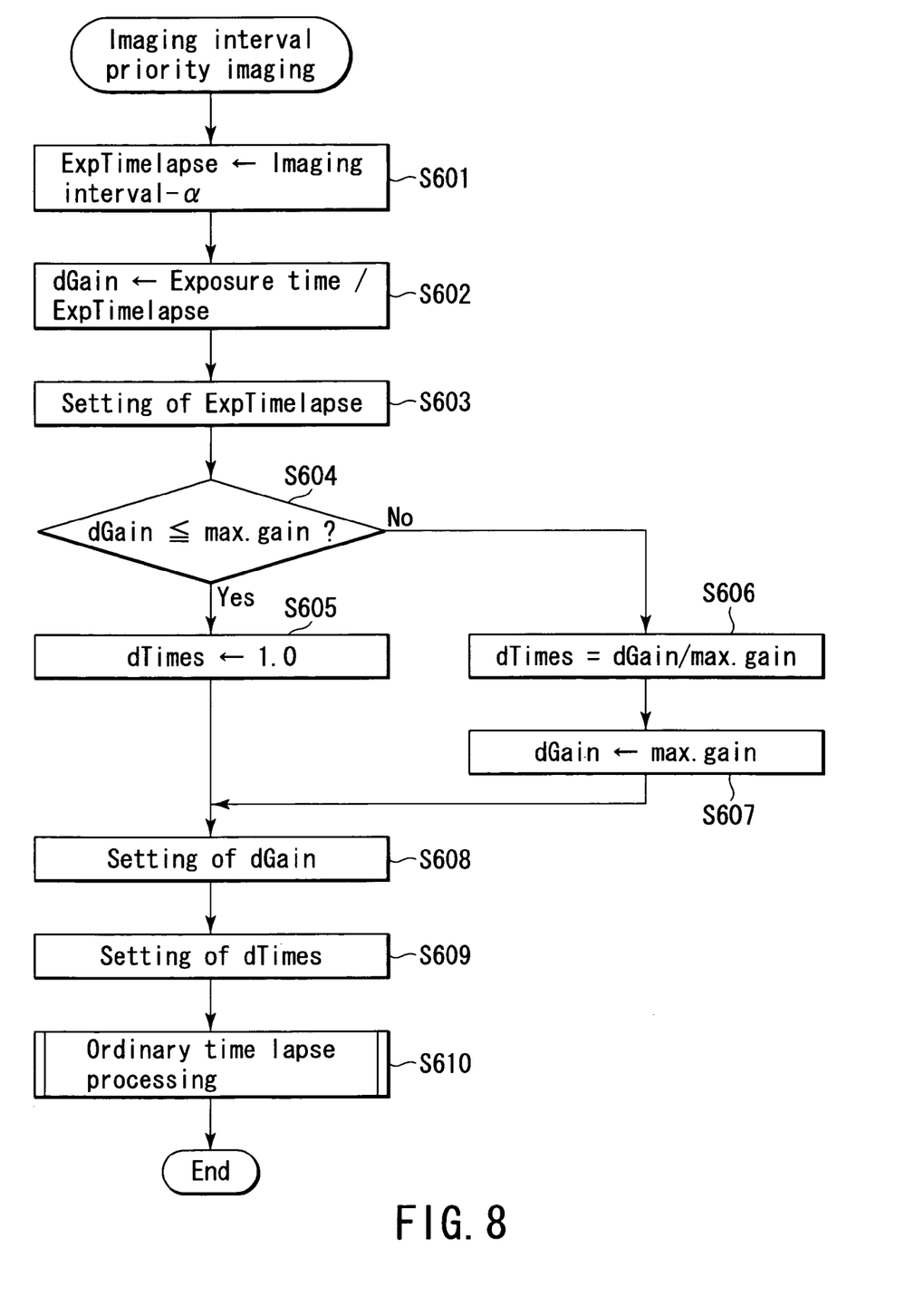
FIG. 8 is a flowchart for explaining an imaging of giving priority to an imaging interval in a third embodiment of the present invention.

In this case, when "process 2" is called in step S110 in FIG. 2, the system controller (CPU) 9 starts imaging interval priority imaging as shown in FIG. 8.

The system controller (CPU) 9 substitutes "imaging interval—$\alpha$" for the variable ExpTimelapse of the exposure time for time lapse imaging, same as in the first embodiment, in the avoiding condition generating portion 903 (step S601).

Next, the system controller (CPU) 9 performs the division formula of the exposure time/ExpTimelapse in the avoiding condition generating portion 903, and puts the obtained result into the coefficient dGain (step S602).

Then, the system controller (CPU) 9 sets ExpTimelapse shortened by putting "imaging interval—$\alpha$" as the exposure time for time lapse imaging in the avoiding condition generating portion 903, in the solid state imaging device driver 3 (step S603).

So far, the process is same as in the first embodiment.

The system controller (CPU) 9, in the avoiding condition generating portion 903, compares the coefficient dGain and the maximum gain that can be set in the preprocess circuit 4, and thereby determines whether or not the condition of dGain$\leq$maximum gain is established (step S604).

Herein, when the condition of dGain$\leq$maximum gain is established, brightness correction by the digital process circuit 5 is not needed, and the system controller (CPU) 9 designates the multiple dTimes of the brightness correcting portion 501 of the digital process circuit 5 at 1 in the avoiding condition generating portion 903 (step S605), and transfers the process to step S608 and thereafter.

On the other hand, if the condition of dGain≦maximum gain is not established in step S604, that is, if the coefficient dGain is larger than the maximum gain that can be set in the gain setting portion 401 of the preprocess circuit 4, it is required to correct the brightness in the digital process 5. Therefore, the system controller (CPU) 9 calculates the brightness correction coefficient in the avoiding condition generating portion 903.

In this case, the system controller (CPU) 9 calculates the division of "dGain/maximum gain that can be set in the preprocess circuit 4", and substitutes the result for dTimes in the avoiding condition generating portion 903 (step S606).

Subsequently, the system controller (CPU) 9 substitutes the maximum gain for dGain in order to set the maximum gain value in the preprocess circuit 4 in the avoiding condition generating portion 903 (step S607).

Consequently, the system controller (CPU) 9 transfers to the process of step S608 and thereafter as mentioned below.

First, the system controller (CPU) 9 sets the dGain determined in the avoiding condition generating portion 903 in the gain setting portion 401 of the preprocess circuit 4 (step S608).

Next, the system controller (CPU) 9 sets the dTimes determined in the avoiding condition generating portion 903 in the brightness correcting portion 501 of the digital process circuit 5 (step S609).

The system controller (CPU) 9 instructs the solid state imaging device 1 to execute imaging by ordinary time lapse imaging (step S610).

Since this process is same as in the foregoing ordinary time lapse imaging, its explanation is omitted.

Therefore, also in the third embodiment, when the operator desires to image by priority given to the imaging interval, if the exposure time set in time lapse imaging is longer than the imaging interval (exposure time>imaging interval), the actual exposure time is changed to less than the imaging interval, and the sensitivity is raised and the time lapse imaging is executed by correcting the brightness of the image by the relation of the imaging interval and the shortened exposure time. Accordingly, the image acquiring device for performing time lapse imaging suited to the purpose of the operator and ease of use can be provided.

Even if the difference between the imaging interval and the shortened exposure time is large, since the sensitivity is raised by correcting the brightness of the image by coefficient multiplication in the digital process circuit 5 further from the state of setting the maximum gain in the preprocess circuit 4, time lapse imaging suited to the purpose of the operation can be realized.

The invention is not limited to the illustrated embodiments alone, but may be changed and modified in various manners, without departing from the true spirit thereof, in the stage of carrying out.

The embodiments include various stages of the invention, and various inventions may be devised by properly combining the plurality of disclosed constituent requirements.

For example, even if several constituent requirements are eliminated from the all constituent requirements disclosed in the embodiments, as long as the same effects are obtained substantially, structures minus several constituent requirements may be also composed as inventions.

As described herein, the invention provides an image acquiring device and method for time lapse imaging capable of selecting an optimum imaging method easily.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image acquiring device for performing time lapse imaging, comprising:

an imaging portion which performs imaging of a subject;

a time lapse imaging condition setting portion which sets a time lapse imaging condition including at least an exposure time and an imaging interval, prior to the imaging of the subject by the imaging portion;

a determining portion which determines a contradiction of the time lapse imaging condition set by the time lapse imaging condition setting portion according to a predetermined criterion; and a presenting portion which presents at least information relating to the contradiction of the time lapse imaging condition based on a determined result determined by the determining portion;

an avoiding condition generating portion which generates a plurality of time lapse imaging conditions for avoiding the contradiction of the time lapse imaging condition based on the determined result determined by the determining portion, and causes information relating to the plurality of time lapse imaging conditions to be presented by the presenting portion;

a selecting portion which selects one of the plurality of time lapse imaging conditions from the information relating to the plurality of time lapse imaging conditions presented by the presenting portion;

an instructing portion which instructs the imaging portion to execute time lapse imaging based on the time lapse imaging condition selected by the selecting portion;

an exposure time setting portion which sets the exposure time set by the time lapse imaging condition setting portion to the imaging portion;

a gain setting portion which enables setting of gain of an output signal from the imaging portion; and a brightness correcting portion which enables correction of brightness of an image by correcting the output signal from the imaging portion;

wherein the determining portion determines the contradiction of the time lapse imaging condition by using a relation between the exposure time and the imaging interval as the predetermined criterion;

wherein, when the determining portion determines as the contradiction that the exposure time is longer than the imaging interval, the avoiding condition generating portion changes a set value of the exposure time set by the exposure time setting portion to be shorter than the imaging interval, and sets a value of the gain set by the gain setting portion to a value determined from a ratio of the exposure time after the change and the imaging interval, and when a set gain value exceeds a maximum gain value, sets the maximum gain value as the value of the gain set by the gain setting portion and sets a value for correcting the brightness of the image by the brightness correction part based on a value determined from a ratio of the value of the gain determined from the ratio and the maximum gain value.

2. The image acquiring device for performing time lapse imaging according to claim 1, wherein the imaging portion comprises an imaging portion of a microscopic image acquiring device.

3. A method for an image acquiring device, which includes an imaging portion which performs imaging of a subject and a presenting portion, the method comprising:
- setting a time lapse imaging condition including at least an exposure time and an imaging interval, prior to the imaging of the subject by the imaging portion;
- determining a contradiction of the set time lapse imaging condition according to a predetermined criterion;
- presenting, via the presenting section, at least information relating to the contradiction of the time lapse imaging condition based on a result of the determination of the contradiction;
- generating a plurality of time lapse imaging conditions for avoiding the contradiction of the time lapse imaging condition based on the result of the determination of the contradiction of the time lapse imaging condition, and presenting information relating to the plurality of time lapse imaging conditions by the presenting portion;
- selecting one of the plurality of time lapse imaging conditions from the information relating to the plurality of time lapse imaging conditions presented by the presenting portion; and
- instructing the imaging portion to execute time lapse imaging based on the selected time lapse imaging condition;
- wherein the predetermined criterion according to which the contradiction of the time lapse imaging condition is determined is a relation between the exposure time and the imaging interval;
- wherein the image acquiring device further comprises an exposure time setting portion which sets the exposure time, which is set by the setting of the time lapse imaging condition, to the imaging portion, a gain setting portion which enables setting of gain of an output signal from the imaging portion, and a brightness correcting portion which enables correction of brightness of an image by correcting the output signal from the imaging portion; and
- wherein, when the exposure time is determined to be longer than the imaging interval as the contradiction, the generating the plurality of time lapse imaging conditions changes a value of the exposure time set by the exposure time setting portion to be shorter than the imaging interval, and sets a value of the gain set by the gain setting portion to a value determined from a ratio of the exposure time after the change and the imaging interval, and when a set gain value exceeds a maximum gain value, sets the maximum gain value as the gain value and sets a value for correcting the brightness of the image by the brightness correcting portion based on a value determined from a ratio of the value of the gain determined from the ratio and the maximum gain value.

4. The method according to claim 3, wherein the imaging portion comprises an imaging portion of a microscopic image acquiring device for fluorescence photography.

5. An image acquiring device for performing time lapse imaging, comprising:
- imaging means for performing imaging of a subject;
- time lapse imaging condition setting means for setting a time lapse imaging condition including at least an exposure time and an imaging interval, prior to the imaging of the subject by the imaging means;
- determining means for determining a contradiction of the time lapse imaging condition set by the time lapse imaging condition setting means according to a predetermined criterion;
- presenting means for presenting at least information relating to the contradiction of the time lapse imaging condition based on a determined result determined by the determining means;
- avoiding condition generating means for generating a plurality of time lapse imaging conditions for avoiding the contradiction of the time lapse imaging condition based on the determined result determined by the determining means, and causing information relating to the plurality of time lapse imaging conditions to be presented by the presenting means;
- selecting means for selecting one of the plurality of time lapse imaging conditions from the information relating to the plurality of time lapse imaging conditions presented by the presenting means;
- instructing means for instructing the imaging means to execute time lapse imaging based on the time lapse imaging condition selected by the selecting means;
- exposure time setting means for setting the exposure time set by the time lapse imaging condition setting means to the imaging means;
- gain setting means for enabling setting of gain of an output signal from the imaging means; and
- brightness correcting means for enabling correction of brightness of the image by correcting the output signal from the imaging means;
- wherein the determining means determines the contradiction of the time lapse imaging condition by using a relation between the exposure time and the imaging interval as the predetermined criterion; and
- wherein, when the determining means determines the contradiction of the time lapse imaging condition in which the exposure time is longer than the imaging interval, the avoiding condition generating means changes a set value of the exposure time set by the exposure time setting means to be shorter than the imaging interval, and sets a value of the gain set by the gain setting means to the value determined from a ratio of the exposure time after the change and the imaging interval, and when a set gain value exceeds a maximum gain value, sets the maximum gain value as the value of the gain set by the gain setting means and sets a value for correcting the brightness of the image by the brightness correction means based on the value determined from a ratio of the value of the gain determined from the ratio and the maximum gain value.

6. The image acquiring device for performing time lapse imaging according to claim 5, wherein the imaging means comprises imaging means of a microscopic image acquiring device.

* * * * *